(12) United States Patent
Ravin et al.

(10) Patent No.: US 9,217,698 B2
(45) Date of Patent: Dec. 22, 2015

(54) DEVICE FOR SIMULATING EXPLOSIVE BLAST AND IMAGING BIOLOGICAL SPECIMEN

(71) Applicant: The United States of America, as represented by the Secretary, Department of Health and Human Services, Washington, DC (US)

(72) Inventors: Rea Ravin, Rockville, MD (US); Paul S. Blank, Gettysburg, PA (US); Alex Steinkamp, Portland, OR (US); Kim Lee Mcafee, Linden, VA (US); Joshua Zimmerberg, Bethesda, MD (US); Sergey Bezrukov, Derwood, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 309 days.

(21) Appl. No.: 13/748,410

(22) Filed: Jan. 23, 2013

(65) Prior Publication Data
US 2013/0186173 A1    Jul. 25, 2013

Related U.S. Application Data

(60) Provisional application No. 61/590,209, filed on Jan. 24, 2012.

(51) Int. Cl.
*G01N 3/30* (2006.01)
*G01N 3/307* (2006.01)

(52) U.S. Cl.
CPC . *G01N 3/30* (2013.01); *G01N 3/307* (2013.01)

(58) Field of Classification Search
CPC .......... G01N 3/307; G01N 3/30; G01N 3/313
USPC ...................................................... 73/12.08
See application file for complete search history.

(56) References Cited

U.S. PATENT DOCUMENTS 4,014,262 A    3/1977 Betts
4,038,961 A    8/1977 Olofsson
(Continued)

FOREIGN PATENT DOCUMENTS

WO    WO 2009/125440    10/2009

OTHER PUBLICATIONS

Yung Chia Chen, Douglas H. Smith, and David F. Meaney, "In-vitro Approaches for studying Blast-Induced Traumatic Brain Injury", journal of Neurotrauma 26:861-876, Jun. 2009.*

(Continued)

*Primary Examiner* — Lisa Caputo
*Assistant Examiner* — Nathaniel T Woodward
(74) *Attorney, Agent, or Firm* — Ari M. Bai; Polsinelli PC

(57) ABSTRACT

A device and method for simulating a blast shock wave of the type produced by explosive devices such as bombs. A pneumatic charge releases a blast shock wave along a conduit which terminates in a first outlet that communicates with the atmosphere and a second outlet that is sealed to a specimen chamber. The first outlet has a quick release valve that prevents venting of the pneumatic charge to the atmosphere until the pressure at the valve reaches a predetermined level that opens the valve. The pneumatic charge therefore initially flows through the second outlet to direct the blast into the specimen chamber, until subsequent opening of the quick release valve redirects the gas flow out of the first outlet and rapidly reduces pressure in the chamber. The blast wave closely simulates the Friedlander curve, and its effects are viewed during instead of only after the blast is completed.

32 Claims, 12 Drawing Sheets

(56) References Cited

U.S. PATENT DOCUMENTS

| | | | |
|---|---|---|---|
| 4,248,080 A * | 2/1981 | Chuck | 73/146.8 |
| 4,282,852 A | 8/1981 | Omana | |
| 4,865,009 A | 9/1989 | Ford et al. | |
| 5,114,140 A | 5/1992 | Barr | |
| 6,439,891 B1 | 8/2002 | Tate et al. | |
| 6,536,258 B1 | 3/2003 | Mostaghel | |
| 6,740,497 B2 * | 5/2004 | Allbritton et al. | 435/15 |
| 7,470,274 B2 * | 12/2008 | Lebet | 606/128 |
| 7,726,124 B2 | 6/2010 | Gram | |
| 7,905,179 B2 | 3/2011 | Brock | |
| 8,079,322 B2 | 12/2011 | Carpenter | |
| 2007/0099294 A1 * | 5/2007 | Yang et al. | 435/299.1 |
| 2008/0190286 A1 | 8/2008 | Gram | |
| 2009/0151465 A1 * | 6/2009 | Alireza | 73/744 |
| 2010/0256957 A1 | 10/2010 | Slavik | |

OTHER PUBLICATIONS

Stanislav I. Svetlov, Victor Prima, Daniel R. Kirk, Hector Gutierrez, Kenneth C. Curley, Ronald L. Hayes, and Kevin K. Wang, "Morphologic and Biochemical Characterization of Brain Injury in a Model of Controlled Blast Overpressure Exposure", The Journal of Trauma, vol. 69, Oct. 4, 2010.*

Michelle C. LaPlaca and Lawrence E. Thibault, "An In Vitro Traumatic Injury Model to Examine the Response of Neurons to a Hydrodynamically-Induced Deformation", Annals of Biomedical Engineering, vol. 25, pp. 665-677, 1997.*

Taylor and Ford, "Simulation of Blast-Induced Early-Time Intracranial Wave Physics leading to Traumatic Brain Injury," *Journal of Biomechanical Engineering*, 131:1-11 (2009).

Chen et al. "*In-Vitro* Approaches for Studying Blast-Induced Traumatic Brain Injury," *Journal of Neurotrauma*, 26:861-876 (2009).

Long et al. "Blast Overpressure in Rats: Recreating a Battlefield Injury in the Laboratory," *Journal of Neurotrauma*, 26:827-840 (2009).

Zhang et al. "Experimental Study of Blast-Induced Traumatic Brain Injury Using a Physical Head Model," *Stapp Car Crash Journal* (Nov. 1, 2009).

Amal Bouamoul "Numerical study of primary blast injury to human and sheep lung induced by simple and complex blast loadings," *Defense Research and Development Canada Technical Report* (Dec. 2009).

Arun et al. "Studies on blast traumatic brain injury using in-vitro model with shock tube," *Cellular, molecular and developmental neuroscience*, 22(8):379-384 (2011).

* cited by examiner

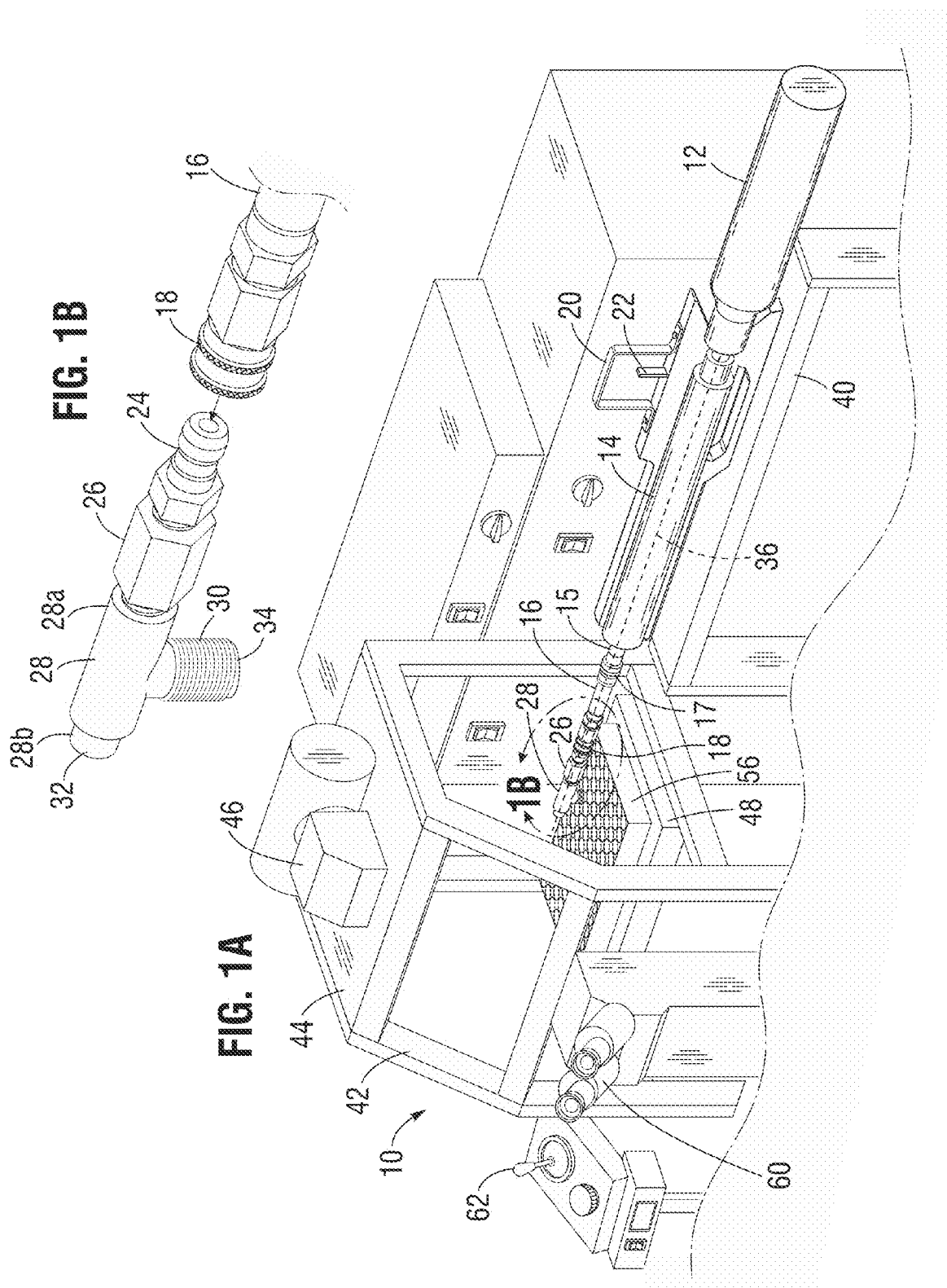

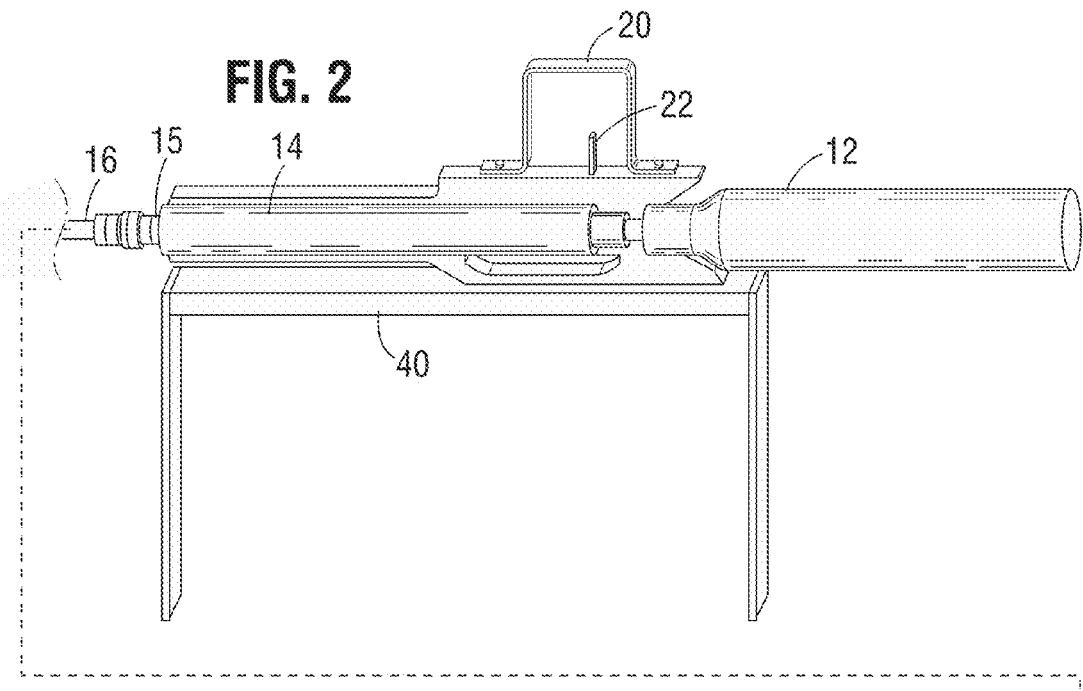
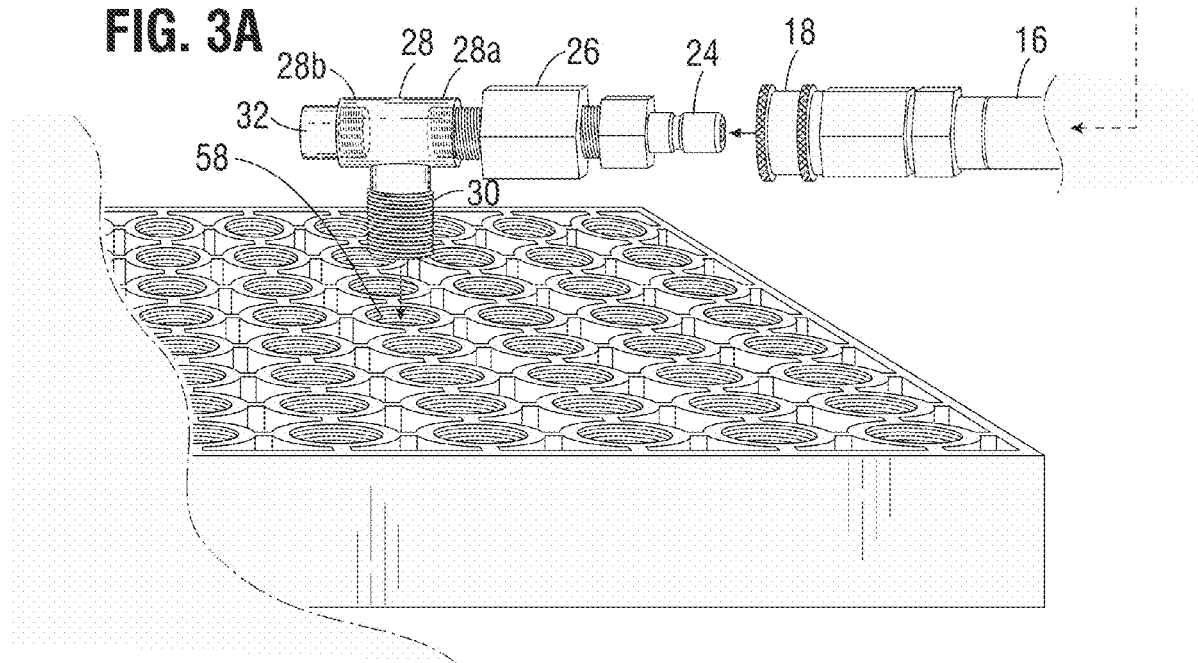

With Shear
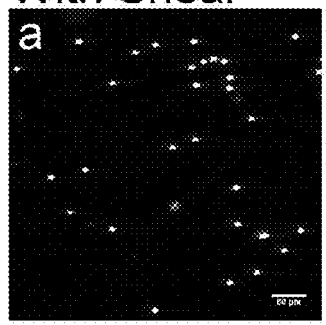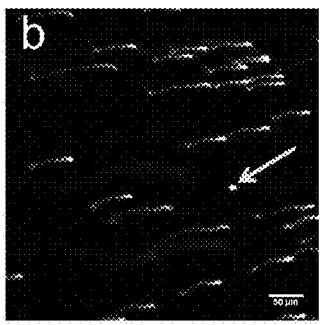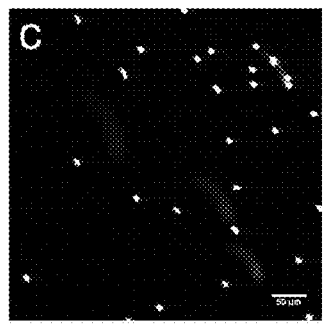
FIG. 6A
Without Shear
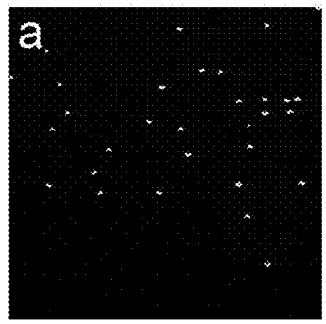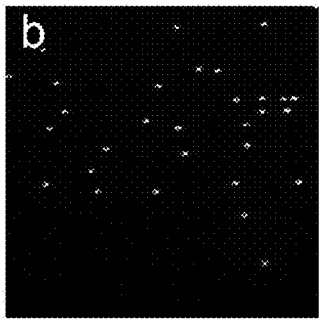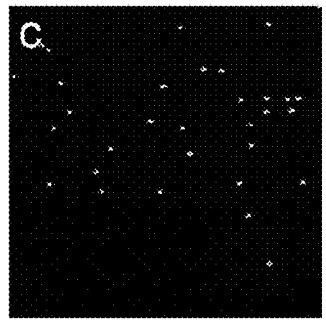
FIG. 6B
− 400 ms     0 ms     + 400 ms

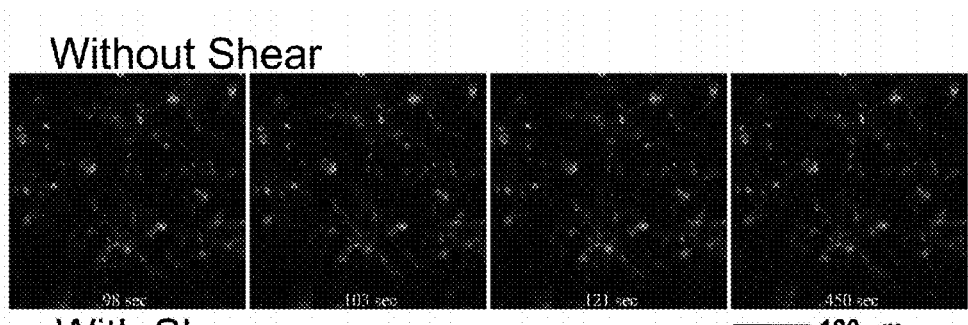
FIG. 7A
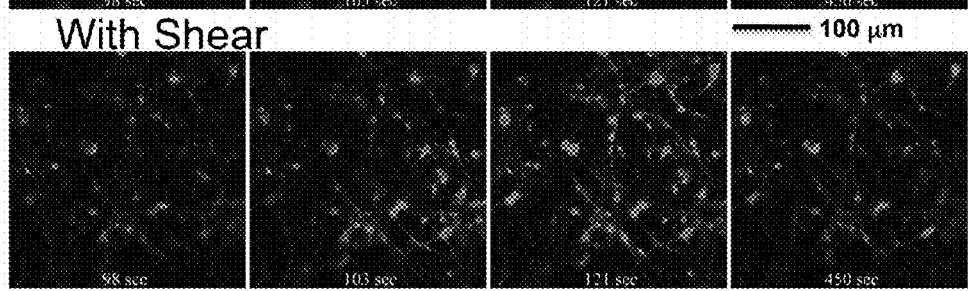
FIG. 7B
FIG. 7C
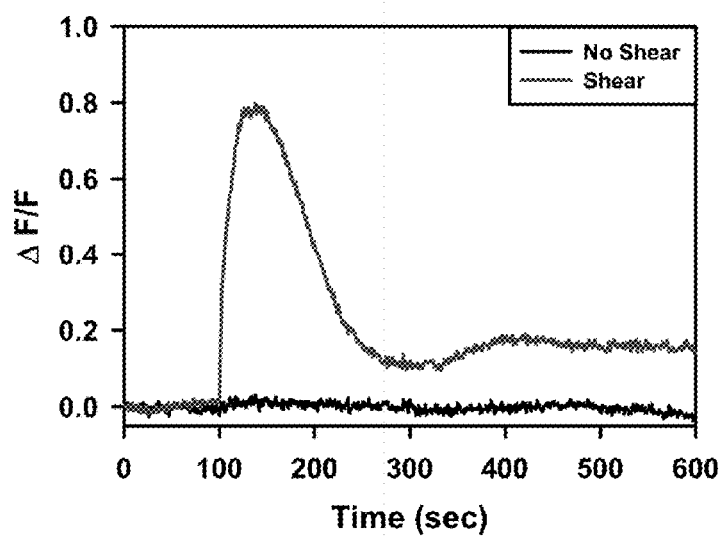

DEVICE FOR SIMULATING EXPLOSIVE BLAST AND IMAGING BIOLOGICAL SPECIMEN

CROSS REFERENCE TO RELATED APPLICATION

This application claims the benefit of U.S. Provisional Application No. 61/590,209, filed Jan. 24, 2012, which is incorporated herein by reference.

FIELD

A blast simulator is disclosed for assessing the effect of an explosion on biological tissue, such as tissue of the central nervous system (CNS).

BACKGROUND

Traumatic Brain Injury (TBI) is a major public health problem. Since 2001, over 150,000 US military personnel have been diagnosed with a mild form of TBI, often after exposure to an explosive blast (bTBI), with a spectrum of neurological and psychological deficits.

The Centers for Disease Control and Prevention (CDC) separates blast injury into four phases. The primary injury phase is the response of brain tissue to the blast wave from an intense over-pressurization impulse of the blast. A secondary injury phase results from shrapnel penetration. Tertiary injury is caused by head contact/acceleration forces as the body is moved by the forced air flow from the blast. A quaternary injury phase is any injury not included in the first three phases, such as hemorrhagic shock or chemical/thermal burn injury.

The primary injury phase, the direct result of the shockwave generated by an explosion, is the least understood. The blast shock wave (BSW) of primary bTBI is a transient, solitary supersonic pressure wave with a rapid (sub-msec) increase in pressure (i.e. compression) followed by a more slowly developing (msec) rarefraction phase of low pressure (i.e. tension). In the majority of bTBI, the peak pressure is low; exposure to blasts estimated to create 10 atm peak pressure in the skull for a few milliseconds can result in death for unprotected persons. Although dynamic compression, tension, and shear stress have all been proposed to explain primary bTBI, the identity of the mechanical forces involved, the tissue-force interaction(s) and the cellular damage properties remain unresolved.

A barotrauma chamber is commonly used to study the effect of pressure on biological tissue, such as CNS tissue. Shepard et al., *J. Surg. Res.* 51:417-424 (1991). The barotrauma chamber applies pressure evenly to all cells or tissue components in the chamber. The pressure wave in a barotrauma chamber can be produced by either hydrostatic or fluid percussion mechanisms.

Extracorporeal shock wave lithotripsy (ESWL) has also been used to generate high-amplitude, transient pressure pulses to study shock-wave induced tissue damage. For example, Howard and Sturtevant used ESWL in vitro on thin membranes immersed in tissue-mimicking fluids to study the mechanism of pulsed pressure tissue damage. *Ultrasound Med. Biol.* 23:1107-1122 (1997). This device permitted the study of pressure-induced compression and lateral extension that induced shear damage to structures such as the plasma membrane, organelles and intracellular membranes.

Shock tubes have also been used to expose cells or even entire bodies to simulated blasts to study how they respond to fast and extreme changes in pressure, as in Arun et al., *Neuroreport* 22:379-384 (2011). A compression-driven shock tube was used to simulate blast effects and subsequently study neuropathological changes in Long et al., *J. Neurotrauma* 26:827-840 (2009). The blast overpressure was generated by introducing pressurized gas into the shock tube until a Mylar membrane ruptured at a preselected pressure.

SUMMARY

Animal studies on the effects of shockwave in vivo are useful for studying aspects of cellular damage mechanisms, but lack the capability for real-time monitoring of cellular behavior during and immediately after the blast, and are unable to differentiate the proposed direct effects of the transient pressure pulse from the secondary effects of the shear stresses produced by that pressure transient. In vitro models of primary blast injury are likewise limited by an absence of real-time, high spatial and temporal detection of cellular responses during, immediately after, and long after the blast, and they do not differentiate shear from pressure effects.

Some of these drawbacks are overcome by the device disclosed herein which simulates an explosive blast shock wave (BSW). The device includes a source of compressed gas and a primary conduit for conveying gas from the source of compressed gas along a primary conduit having a primary axis of gas flow. The primary conduit terminates in a release valve that opens when gas pressure at the release valve reaches a predetermined pressure. A secondary conduit extends at an angle (not parallel) to the primary conduit axis of gas flow and the secondary conduit terminates in an outlet orifice that directs gas from the primary conduit toward a target region such as a microscope stage. The secondary conduit is joined to the primary conduit between the source of compressed gas and the quick release valve.

A trigger releases the compressed gas into the primary conduit toward the release valve to generate a simulated blast shock wave flow of gas that is blocked by the release valve and therefore flows at an angle through the secondary conduit and the outlet orifice toward the target. The pressure amplitude of the blast shock wave increases until the release valve in the primary conduit opens and allows the gas to flow along the longitudinal axis of the primary conduit over the opening to the secondary conduit. The flow of the blast shock wave past the secondary conduit rapidly reduces the pressure within the secondary conduit and at the outlet orifice to mimic the rapid blast shock wave pressure reduction of an actual explosion. In some embodiments, the flow of gas over the secondary outlet generates negative pressure at the outlet orifice. In some embodiments the secondary conduit extends substantially perpendicular to the primary axis of gas flow through the primary conduit to maximize this effect.

In some embodiments a specimen platform is fixed adjacent the outlet orifice in the flow path of the blast shock wave as the shock wave emerges from the outlet orifice of the secondary conduit. An imaging device is provided to capture images of the specimen and determine its response before, during and after the blast shock wave. For example, the imaging device may include a video camera and/or a microscope. In other embodiments the specimen is contained in a transparent chamber on a transparent platform and the microscope is positioned to view the specimen from below the platform. In specific embodiments, the chamber is the well of a multiple-well plate that is securely fixed to a microscope stage. Different depths or volumes of liquid in the chamber expose the specimen to varying levels of shear stress, so that the effects of different levels of shear stress on the biological specimen can be measured.

The quick release valve can take many forms, such as a plug or other occlusion member that is ejected from the primary conduit when pressure at the outlet orifice reaches a predetermined maximum value that approximates the maximum pressure of an explosive blast. A coupling may be provided to connect the secondary conduit to the chamber in which the specimen is contained so that the simulated blast shock wave is directed substantially only into the chamber that contains the sample. In one embodiment, mating threads on the secondary conduit and in the chamber couple them to one another in a substantially sealed relationship to direct the blast shock wave substantially only into the specimen chamber until the quick release valve opens.

In other embodiments, the specimen platform is movable to position a plurality of different specimens over the imaging device, such as the objective lens of a microscope. A multiple-well plate can be placed on the specimen platform and tissue samples or cellular preparations can be placed in different wells on the plate. The device is particularly adapted for studying nerve cells in the wells of the plates that are exposed to the blast shock wave.

The disclosed device is capable of imaging and/or analyzing images of target tissue over time as blast injury occurs, instead of being limited to the assessing end point damage after a simulated blast is finished. For example, the device is capable of viewing cellular or tissue responses of a biological specimen to a blast shock wave as the shock wave progresses, instead of being limited to an assessment of the effects after the simulated blast is completed. Although a variety of tissues and cells can be studied using this device, the disclosed embodiment is described with reference to the analysis of the response of cultured nerve cells to the blast wave. The disclosed device is also capable of substantially reproducing the Friedlander curve blast shock wave pressure profile to better model the effects of a blast on biological specimens.

BRIEF DESCRIPTION OF THE DRAWINGS

FIG. 1A is a perspective view of a device for generating a blast shock wave for studying the effect of the blast shock wave on biological specimens as the blast shock wave is in progress. FIG. 1B is an enlarged perspective view of a portion of FIG. 1A, showing a quick connect mechanism between a high pressure hose and a T-connector for generating the blast shock wave through the T-outlets.

FIG. 2 is a side view of an air gun that generates pneumatic pressure for simulating the blast shock wave.

FIG. 3A is an enlarged perspective view of the T-connector having T-outlets through which the blast shock wave is generated, and the threads that mate to couple the device to a well of a multiple well plate.

FIGS. 6A and 6B are a series of digital images that depict bead movement in a specimen chamber with shear (FIG. 6A) and without shear (FIG. 6B). The images were obtained from three consecutive frames of 400 msec duration captured beads before (a), during (b), and after (c) the application of a ~11 atm peak pressure blast with shear (180 µl fluid volume, FIG. 6A) and without shear (380 µl fluid volume, FIG. 6B). Significant bead motion due to shear is registered in top frame FIG. 6A frame b, in which only a single bead did not move (arrow). The immobile bead was presumably immobilized due to adhesion to the surface, and provided a reference to check for stability of the specimen platform during the blast. In the absence of shear (with a 380 fluid volume), the application of the same peak pressure blast does not show any bead displacement (FIG. 6B frame b).

FIG. 7A shows sequential fluo-4 calcium imaging of a dissociated primary human fetal CNS cell culture without shear (380 µl well fluid volume); the blast occurred at time 100 seconds. FIG. 7B shows sequential fluo-4 calcium imaging of the same cells as in FIG. 7A but with shear (150 µl well fluid volume) using the same blast parameters; the blast occurred at time 100 seconds. FIG. 7C is a graph of $\Delta F/F$ versus time for the cells shown in FIG. 7A and FIG. 7B for 10 minutes before, during, and after the blast.

The features and advantages of the invention will become more apparent from the following detailed description, which proceeds with reference to the accompanying figures.

DETAILED DESCRIPTION

Devices and methods are disclosed herein for determining responses of biological tissue, such as cultured cells, to simulated blast shock waves. The device is capable of viewing cellular or tissue responses of a biological specimen to a blast shock wave as the shock wave progresses, instead of being limited to an assessment of the effects after the simulated blast is over. Although a variety of tissues and cells can be studied using this device, the disclosed embodiment is described with reference to the analysis of the response of cultured nerve cells to the blast wave. The disclosed device is also capable of accurately substantially reproducing the Friedlander curve blast shock wave pressure profile.

Abbreviations

BSW: Blast shock wave

CNS: Central nervous system bTBI: Blast-induced traumatic brain injury

Terms

Unless otherwise noted, technical terms are used according to conventional usage. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). In case of conflict, the present specification, including explanations of terms, will control. In addition, the materials, methods, and examples are illustrative only and not intended to be limiting.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise.

To facilitate review of the various embodiments of this disclosure, the following explanations of terms are provided:

Angled or at an angle to: not parallel to; at an angle of 1-179 degrees to a reference structure or axis. Includes structures that are substantially perpendicular to one another (such as at an angle of 80-100 degrees, for example 85-95 degrees, or 90 degrees).

Blast shock wave: a pulse of pressurized gas that is produced by an explosion of an explosive device. The pulse can either be produced by an explosion of an actual explosive device, or it can be simulated. The pulse profile of the blast shock wave is generally described by the Friedlander curve.

Figure 5:
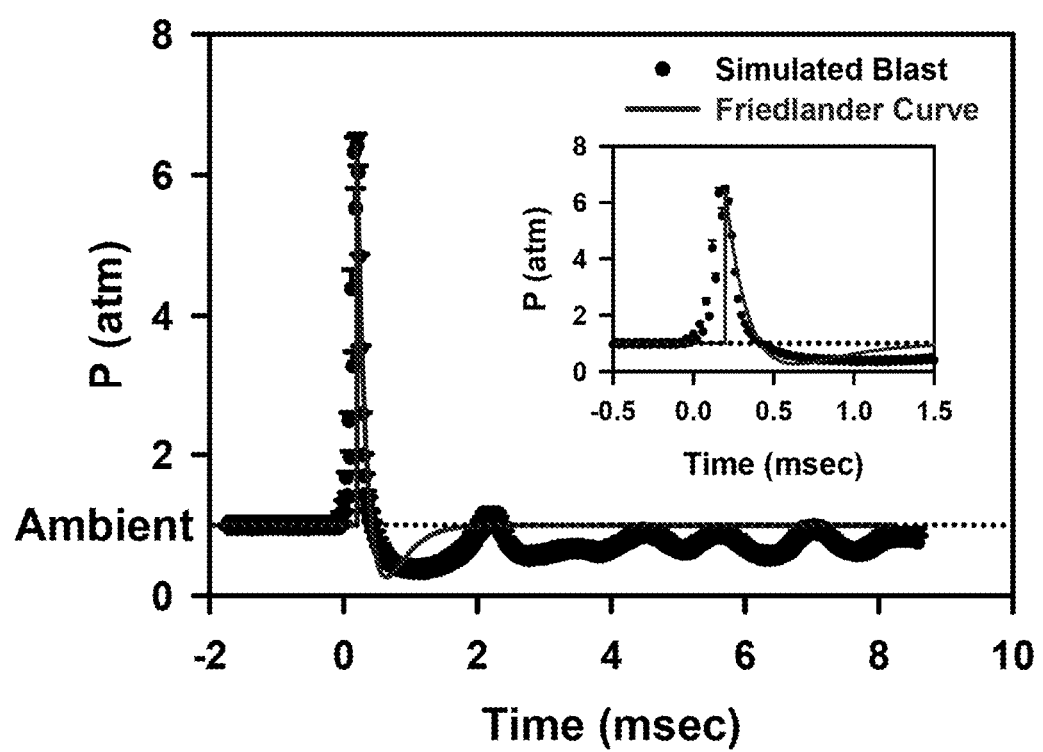
FIG. 5 is a pressure profile measurement of the simulated open field blast shockwave compared to a classical Friedlander curve of the same peak pressure and positive phase duration. An average of 6 measurements is shown with standard error.

Friedlander curve: Most conventional high explosives release, in a relatively short amount of time, a large quantity of energy through expansion of the gaseous detonation products. This energy release results in an overpressure wave that travels through the air at a velocity greater than the speed of sound. As the blast wave propagates away from the center of the explosion, its energy spreads through an increasing volume of air and the blast magnitude decreases rapidly. The passage of the blast wave through a particular position away from the detonation can be characterized as a simple or a complex blast wave. A simple blastwave pressure disturbance resulting from an ideal explosion in free field has the shape of a Friedlander curve. Ideal explosions are defined as being produced by uncased bare charges, made with a conventional explosive (e.g. TNT, C4, RDX) with either aspherical or a hemispherical geometry. In the Friedlander curve, the pressure is comprised of a positive phase and a relatively long negative pressure phase as shown in FIG. 5.

Specimen: Biological material, such as a tissue specimen or cellular preparation in which cells may be present in a medium for nurturing the cells.

T-outlet: A conduit that is generally T-shaped and has two generally collinear arms and a substantially perpendicular leg, wherein each of the arms and leg terminate in an outlet. A particular example of a T-outlet is a T-connector.

Trigger: a device to release gas from a pressurized source of compressed of gas; the trigger can be mechanical, electrical, electromechanical, or any other combination or type of device that initiates the release. The trigger can be programmed to release the gas at varying rates and maximum amplitudes. The device disclosed herein is adapted to simulate a blast shock wave, such as the type produced by a battlefield explosive device, such as an improvised explosive device (IED). The blast shock wave produced by the device is capable, for example, of generating a simulated blast shock wave at a biological target (for example in a specimen chamber) of at least 4 or 6 atmospheres above the starting pressure (ambient) in less than one milliseconds. In some embodiments, the device produced a blast shock wave in the specimen chamber of 4-15 atm above ambient pressure, for example 6-14 atm above ambient pressure, in less than 0.5 or 0.25 milliseconds, or 0.1 milliseconds with a rapid decrease in pressure in the specimen chamber to the ambient or below ambient pressure. In illustrated examples, the increase of the pressure in the specimen chamber to its maximum amplitude and then the decrease to ambient or below ambient pressure occurs in less than about 0.5 milliseconds. FIG. 5 illustrates examples of blast waves generated by the illustrated device in which the total blast duration from initiation to sub-ambient pressure is less than 1 milliseconds, for example less than 0.5 milliseconds.

In disclosed embodiments, the device is also capable of real-time observation of in vitro responses of biological tissue to the blast shock wave, including microscopic observation and analysis of cellular preparations, such as cultured cells. Examples of nerve tissue that can be studied are tissue of the central nervous system (CNS) which includes the brain and spinal cord, and the peripheral nervous system (PNS) which includes nerve fibers, aggregates of nerve cells, glia and ganglia. Suitable specimens for study with the device disclosed herein include any type of nerve tissue, either a cellular preparation in cell medium or an intact tissue specimen such as a tissue section of brain. Various types of cells that can be cultured, and media and methods for suspending and/or culturing such cells, are described in Banker and Gosslin, *Culturing Nerve Cells*, Cellular and Molecular Neuroscience (1998).

In addition to nerve tissue, other types of tissue (and/or their component cells) can be used as biological specimens in the device disclosed herein. For example, any animal tissue can be used, such as connective, muscle, nervous or epithelial tissue. Tissue from any organ may similarly be used, such as tissue from the brain, kidney, heart, liver, lung, gastrointestinal tract, spleen, skin, ovary, testes, or muscle. Isolated cells from these tissues may also be used, for example brain cells.

In a particularly disclosed embodiment, FIG. 1A shows a device 10 for simulating an explosive blast shock wave (BSW). Device 10 includes a source of compressed gas in the form of a canister 12 connected to an air gun 14, such as an Airforce Model R9901 pre-charged pneumatic air rifle. The gas in the canister is a mixture of 95% air and 5% $CO_2$ pressurized to 1500 psi. The commercially available air gun 14 was modified to replace the inner gun barrel with a chromium-molybdenum steel tube 15 that extends beyond the barrel and terminates at its free end in a quick connect valve member 17 (FIG. 1B) that connects a flexible high pressure hose 16 (capable of withstanding pressure up to 5000 psi) to a second quick connect valve member 18. A further modification was to modify the hammer and spring mechanism that controls the hammer trigger to instead provide a U-bracket 20 on top of air gun 14 with a trigger 22 mounted inside bracket 20. Trigger 22 releases the blast of pneumatic air released from canister 12 to simulate blast shock waves. The force, duration or amplitude of the pressure wave can be varied, for example, by increasing or decreasing the pressure in the canister or changing the diameter of the outlet valve, the strength of the spring in the gun, tension on the spring, or the weight of the hammer in the trigger.

The quick connect valve member 18 is similar to valve member 17, hence only valve member 18 is described in detail (FIG. 1B). Valve member 18 includes a female member that connects to the male member 24 of the quick connect valve to efficiently connect and disconnect members 18 and 24. An axially displaceable collar on member 18 is capable of rapidly disengaging members 18, 24. Male member 24 is threadably engaged to a coupling 26 having internal threads engaged to external threads on male member 2. An opposing end of coupling 26 is externally threaded to mate with internal threads of stainless steel T-connector 28 available from Mcmaster.com. The T-connector 28 has internally threaded proximal arm 28a and internally threaded distal arm 28b, and an externally threaded leg 30 that is angled at a non-parallel angle from the arms of T-connector 28, for example at an oblique or substantially perpendicular angle (80-100 degrees) to a linear axis through the arms of the T-connector 28. The open bottom end of leg 30 forms an outlet orifice 34 through which a blast shock wave from device 10 is emitted during use. Leg 30 may be connected to a specimen well as subsequently described to provide a sealed chamber so that as pressure increases in the specimen well the pressure in the primary conduit also increases.

A quick release valve 32 in arm 28B of T-connector 28 provides a mechanism for venting pressure from the T-connector when a predetermined pressure wave amplitude is reached at valve 32. The valve 32 includes an occlusion member, such as a plastic filter tip taken from a 1250 µl pipette tip (Thermo Scientific). The filter tip has a smooth surface that is not externally threaded, but the occlusion member is made of a material that deforms as it is rotated into internally threaded arm 28b. The filter tip is inserted into the internally threaded arm 28b of T-connector 28 (FIGS. 1B, 3A, 3B and 4) rotates a preselected number of turns (⅙ to 1¼ turns). The number of rotations of the plug into the threads correlates with varying peak overpressure amplitudes, and the plug therefore provides reproducible overpressures to simulate blasts of different intensities. The peak overpressure was varied reproducibly from 6-15 atm above ambient pressure using the specified number of turns so that the plug would be displaced at a predetermined pressure inside T-connector 28. The plug provides a simple quick release valve to achieve a more rapid pressure release as compared to other fixed pressure release valves with longer rise times. In the illustrated embodiment, ⅙ rotation provided 6 atm of release pressure, ⅓ rotation provided 11 atm, and 1¼ turn provided 14 atm maximum pressure before the plug was ejected at the preselected peak overpressure.

Figure 4:
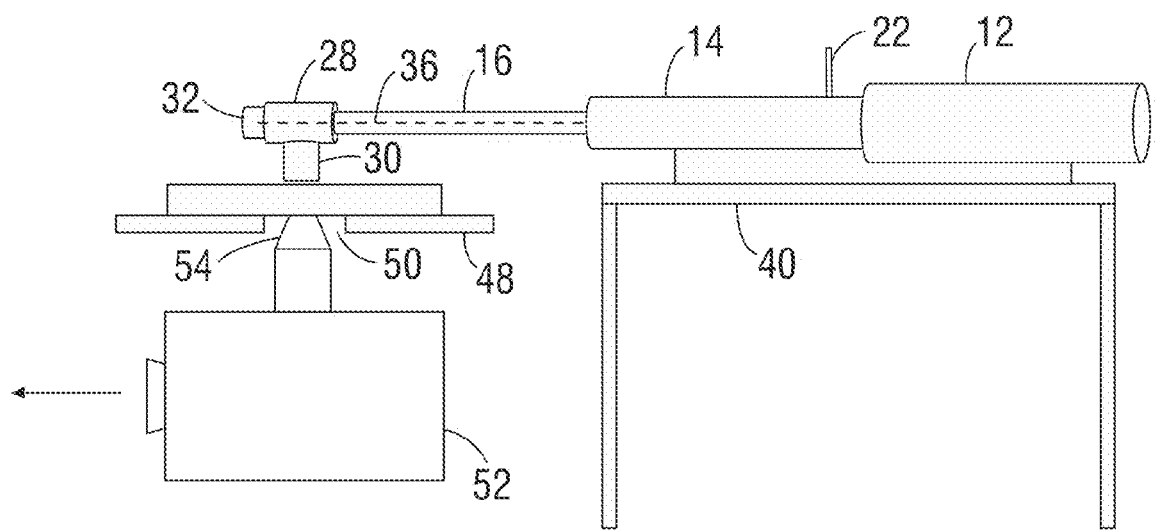
FIG. 4 is a schematic side view illustrating the device and its use with a microscope for real-time observation of cellular responses to an explosive blast.

As shown in FIG. 1A, tube 15, valve 17, hose 16, valve 18/24, coupling 26 and the arms 28a, 28b of T-connector 28 provide an unobstructed primary conduit for conveying gas from canister 12 along a substantially linear primary conduit axis 36 of gas flow that terminates at arm 28b of T-connector 28. FIG. 4 illustrates a simplified schematic view of the primary conduit illustrating the linear primary conduit axis 36 of gas flow as it moves from air gun 14 to the occlusion of quick release valve 32 which is capable of stopping the flow of gas until the gas pressure at valve 32 reaches the predetermined pressure. Although the illustrated embodiment shows a flow along a linear primary conduit axis, the axis can be curved or otherwise non-linear. Leg 30 provides a separate secondary conduit that communicates with the primary conduit such that gas from the primary conduit can flow freely without obstructions into the secondary conduit.

When air gun trigger 22 is activated, device 10 releases a burst of pressurized gas from canister 12 and directs it through the primary conduit along primary conduit axis 36. As the pressurized gas is released, the quick release valve on the T-connector traps gas to redirect a portion of the gas flow away from the primary conduit axis, for example at an angle through the secondary conduit (leg 30 and outlet orifice 34) downwardly toward a sealed specimen well, so that a rapid increase in pressure occurs within the well that simulates a blast pressure wave. Pressure in the primary conduit also continues to increase, and when the pressure in the primary conduit exceeds the limit of the quick release valve the plug is ejected, allowing the gas to escape to the atmosphere through leg 28b, which results in a rapid decay of overpressure as the accumulated pressure is released. The rapid gas flow through the narrow horizontal portion of the T-connector creates a drop in pressure at the outlet orifice 34 of leg 30 to below ambient levels using the Venturi effect. The rapid flow of gas through the primary conduit over the open secondary conduit and out the open end of the primary conduit into the atmosphere causes a rapid decrease in pressure in the sealed well to simulate in the well the rapid pressure decrease a target (such as a person) experiences as a blast shock wave passes the target.

Device 10 is adapted for use in real time monitoring and microscopic evaluation of tissue, for example cellular tissue such as cultured cells, for example cultured nerve cells. Alternatively, intact tissue sections can be used. As shown in FIGS. 1A, 2 and 4, device 10 includes a stationary support beam 40 on which air gun 14 is mounted to avoid recoil of the air gun during pneumatic discharge. Support beam 40 is positioned adjacent microscope carriage 42 having a solid top wall 44 on which is schematically shown a light source 46 that uses an arm to illuminates the interior of carriage 42. Within carriage 44 is a movable motorized stage 48 that moves in a plane parallel to wall 44. Motorized stage 48 has a central aperture 50 (FIG. 4) positioned above a real time imaging apparatus 52. In the disclosed embodiment, real time imaging apparatus 52 is a Ti wide-field inverted microscope for data acquisition and experimental control. FIG. 1A illustrates a 20× air objective (NA 0.75) 54 for imaging the specimen by positioning objective 54 below aperture 50 in motorized stage 48. The imaging device is capable of imaging the view through the microscope, transmitting the image to a viewer, and/or recording the image. Direct visualization of the biological specimen is also possible by viewing the target through eyepieces 60 of the microscope.

The fluorescence indicator Fluo-4 (Invitrogen) was used to monitor intracellular calcium. Fluo-4 was excited using 480 nm light (Chroma HQ 480/40 nm filter) emitted through aperture 50 from below stage 48, and fluorescence emission data was collected (Chroma HQ 535/50 nm filter) during an exposure time of 80-100 msec. The image acquisition rate was 1 Hz. The external isolation box (Oko Lab) maintained temperature (37° C.) and blocked ambient light. A transparent plastic multi-well plate, such as a transparent ninety-six well plate, was mounted on microscope stage 48 using a clamp (not shown) to serve as a specimen platform 56. The clamp fixed the ninety-six well plate firmly to microscope stage 48 to avoid vibration during blast simulation. The microscope condenser was removed to allow access for connecting the pneumatic device to specimen platform 56.

Figure 3B:
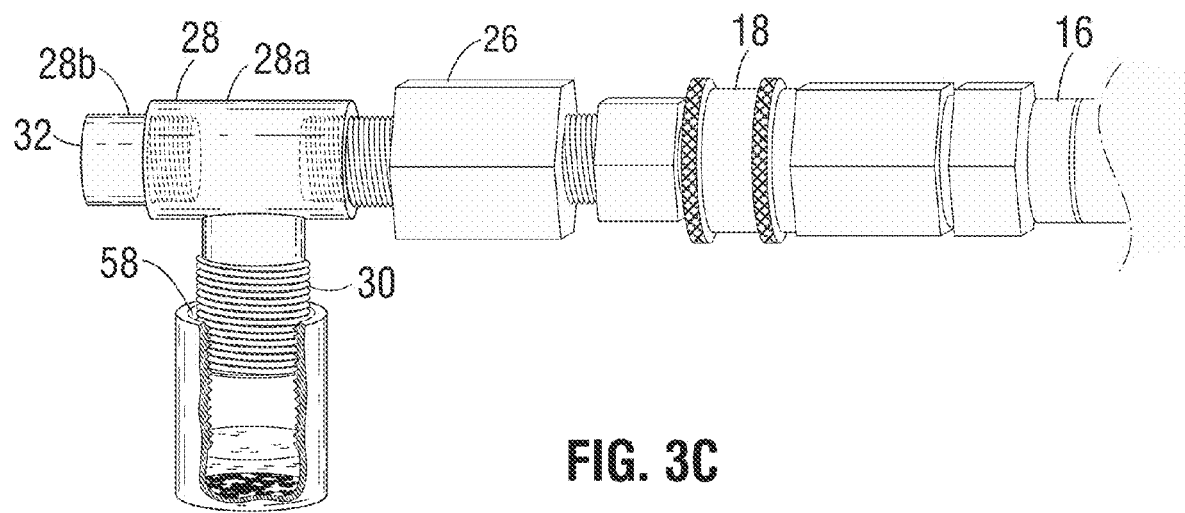
FIG. 3B is an isolated view showing the leg of the T-connector coupled to the well with mating threads on the T-connector and well.

Specimen platform 56 is movable to a location to be impinged by the simulated blast shock wave as it is emitted through outlet orifice 34 so that imaging apparatus 52 views a biological specimen on the illuminated specimen platform as the simulated blast shock wave from outlet orifice 34 impinges the specimen. To isolate the blast shock wave and assess its effect on a particular biological specimen (such as nerve cells layered on the bottom of a well and covered with cell medium) a specimen chamber (such as a well 58 of the multiple-well plate shown in FIGS. 3A and 3B) is provided on the specimen platform. Leg 30 of T-connector 28 is coupled in a substantially sealed relationship to the specimen chamber to allow the blast shock wave to be directed at substantially only the specimen in the specimen chamber. The particular coupling illustrated in FIGS. 3A and 3B is achieved by providing internal spiral threads on the interior wall of well 58 that mate with the external spiral threads of leg 30. The external threads of leg 30 are screwed into the threads on the interior wall of well 58 to fix leg 30 to well 58 in a substantially fixed and sealed engagement.

In use, a biological specimen (such as nerve cells in or covered by cell medium) that is to be exposed to the blast shock wave is placed in a well 58 (FIG. 3B) of specimen platform 56 (FIG. 4). Well 58 is then moved to one of a plurality of positions above objective 54 (FIG. 4) by manipulating a control stick 62 (FIG. 1A) that controls motorized stage 48. Once the specimen chamber is in position over the microscope, then the primary conduit can be assembled by connecting hose 16 to the quick release valves. Threaded leg 30 (FIG. 3B) is screwed into threaded well 58 to form an isolated chamber into which the blast shock wave is to be directed. The volume and/or depth of cell medium or other liquid in chamber 58 can be varied to control the amount of shear force experienced by cells layered on the bottom of the well. Trigger 22 (FIG. 4) is actuated to release a preselected pneumatic charge from canister 12 that simulates a blast shock wave of an explosion (for example from an improvised explosive device) that could cause an injury, such as a blast-induced traumatic brain injury (bTBI). The blast shock wave then travels from air gun 14 along primary conduit axis 36 (FIG. 4) through the primary conduit 14, tube 16, valves 18, 24, coupling 26 and arms 28a, 28b of T-connector 28.

The simulated blast shock wave impinges against the occlusion member of quick release valve 32 to impede the flow of the wave and redirect it into leg 30 and through outlet orifice 34 into the well 58. As the pressure in T-connector 28 increases to a maximum preselected amplitude, the occlusion member of valve 32 overcomes the resistance that has maintained it engaged with the internal threads of arm 28b so that the occlusion member is forced out of arm 28b to open arm 28b to the atmosphere. The flow of the blast wave then vents through arm 28b to the atmosphere. As the gas now rapidly flows in the direction of axis 36 over the open top of leg 30, the pressure in leg 30 and well 58 is rapidly reduced by a Venturi effect that quickly reduces the pressure in well 58 below the original baseline pressure in the well, to simulate the waveform of a Friedlander curve.

The disclosed device can therefore be used in methods of assessing a response of tissue or cells to a simulated blast shock wave by positioning a specimen on the specimen platform adjacent outlet orifice 34, and activating trigger 22 for selectively releasing the compressed gas into the primary conduit formed by air gun 14, tube 16, valves 18, 24, coupling 26 and arms 28a, 28b of T-connector 28. A flow of gas moves through the primary conduit and out of outlet orifice 34 to produce the simulated blast shock wave that impinges the specimen. The effect of the blast shock wave on the specimen can then be observed, for example by viewing a recording of the effect of the shock wave on the specimen. Since the specimen is being observed through a microscope, changes can be detected that would not otherwise be visible to the unaided vision.

An image of the specimen enlarged by a microscope can be viewed in real time through microscope eyepieces 60 (FIG. 1A), or the response of the specimen to the blast shock wave can be viewed on a video screen (not shown). The video screen can display the image either as it occurs, or preferably as a play-back of a recorded image, for example by viewing stop frames of the recorded image at different time points of interest.

The following Examples illustrate the uses and advantages of the disclosed embodiment of the device.

Example 1

Blast and Shear Conditions

Figure 3C:
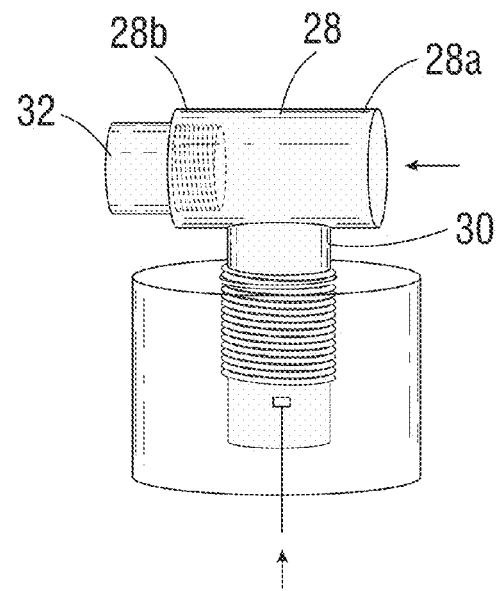
FIG. 3C is a schematic illustration of a device that can be substituted for the T-connector of FIG. 3A to measure pressures generated by the device.

As shown in FIGS. 1A and 3B, leg 30 of T-connector 28 of device 10 was attached to one of the ninety-six wells of platform 56 on the motorized microscope stage 48. Using control stick 62, well 58 was positioned over aperture 50 (FIG. 4) of stage 48 and over the microscope objective lens 54 of imaging apparatus 52. The amplitude of the pressure transient (maximum pressure amplitude) produced by pneumatic discharge of device 10 was varied by altering the number of turns of adjustable quick release plug into internally threaded arm 28b (FIGS. 1A, 1B, 3A 3B and 4). The pressure waveform characteristics produced in chamber 58 by this device were comparable to those recorded at a subject target in open field blasts; the pressure waveform profile in chamber 58 closely resembles a classic Friedlander curve (FIG. 5). Friedlander curves are described in more detail in Brode et al., Blast Wave from a Spherical Charge, *Physics of Fluids*, 2:217-229 (1959). The simulated blasts were generated with rise times in the 0.1 msec range before valve 32 opened, and a two component falling phase: a fast component dropping below ambient pressure within 0.5 msec, and a slower component returning to ambient pressure within 2 msecs (FIG. 5). Pressure transient pressures having maximum amplitudes from 6-15 atm were examined by varying the number of rotations of the plug into the threads of T-connector arm 28b. Differing preselected pressure amplitudes can readily be selected by varying the number of rotations of the plug and measuring pressure transient amplitudes produced thereby. Pressures generated in the wells can be measured using a fiber optic pressure sensor on the interior wall of leg 30 (as in FIG. 3C).

Each blast created not only a fast transient pressure wave, but also shear forces originating at the interface of the gas and liquid. To control the magnitude of shear forces at the cell surface, the well volume was manipulated as larger media volumes increased the distance between cells and the gas-liquid interface, thus reducing the shear forces acting on the cells. To measure the shear forces within the cell plane (generally at the bottom of the well), fluorescent beads (Molecular Probes L-14822 component E) were used as reference markers on the bottom of wells with varying fluid volumes and subjected to blast shocks (peak pressure 11 atm). Beads in wells containing 150 and 180 µl exhibited fast motion in response to a blast (FIG. 6A, With Shear) but beads in 380 µL exhibited no motion with blast (FIG. 6B, Without Shear). Hereinafter, these two volume ranges will be referred to as with and without shear, although the specified volumes are only specific examples of how shear was induced and avoided. Once shear forces at the cell plane are calibrated for a particular experimental system, then the volume of depth of liquid in well 58 can be used to selectively control shear pressure on the cells during subsequent experimentation.

Figure 10A:
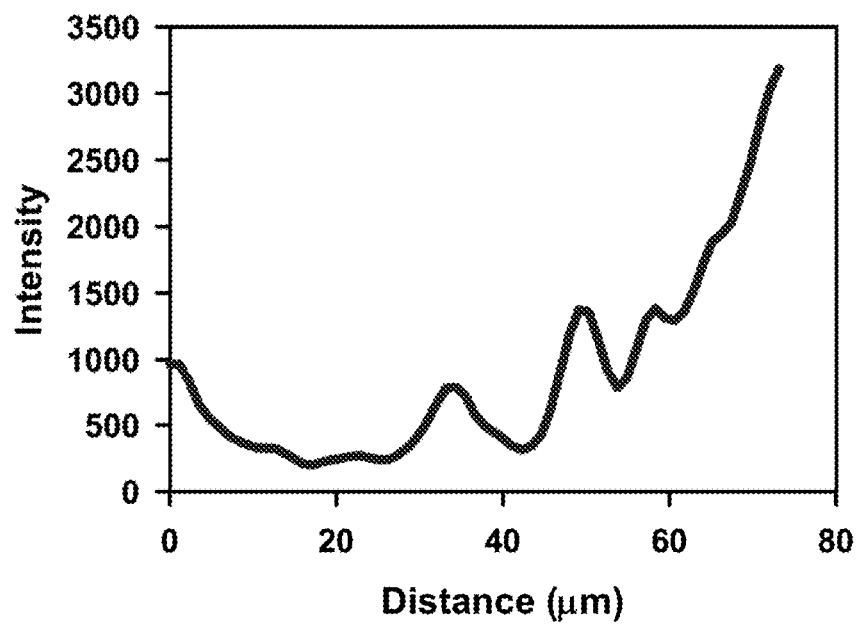
FIG. 10A illustrates intensity vs. trajectory length (Distance) for a moving bead captured in one image frame (see FIG. 6).
Figure 10B:
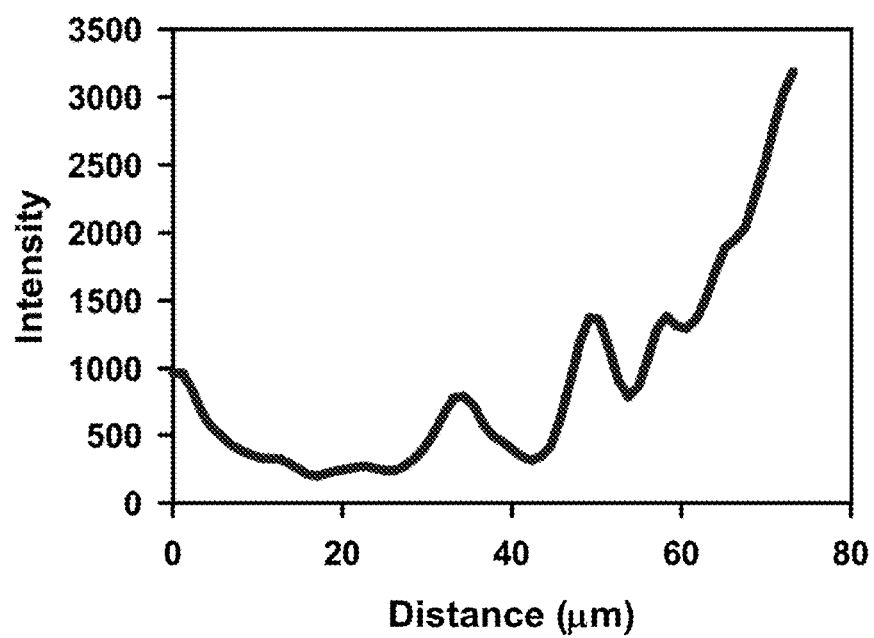
FIG. 10B illustrates time dependent trajectory length (Distance) vs. Time calculated using equations 2 and 3.
Figure 10C:
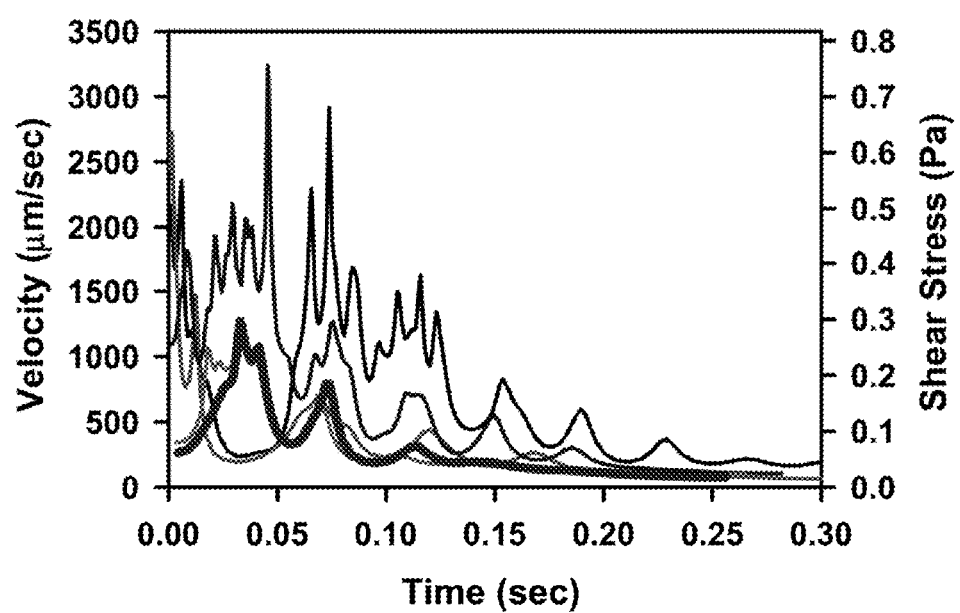
FIG. 10C illustrates velocity and shear stress derived from the derivative of the time dependent trajectory length (thick red curve) and four other representative examples.

Analyzing only those trajectories that were two-dimensional and had no self- or inter-crossings, an estimate of the shear stress during a significant part of the impulse was calculated and found to be ~0.2 Pa averaged over 70 msec with peak shear stress<1 Pa (FIG. 10C). In all measurements without shear the velocities and stresses were lower than the lowest shear that could be estimated by the disclosed technique, <0.0001 Pa. Although this example has been illustrated with particular volumes of liquid in a cylindrical well that is 0.6 cm in diameter, other volumes and depths of different liquids could be used and shear measured using the fluorescent bead assay described in this example. In particular embodiments, a volume/depth of liquid that produces no shear would be selected that produces less than 1 Pa, and particularly less than 0.0001 Pa., and shear forces above 1 Pa. would be selected for measuring shear effects on cells using the fluorescent bead methods disclosed in this example. Different volumes and depths of different liquids can be chosen to measure different shear stress effects on the specimen, once initial calibration of the system has been performed as described in this example.

Example 2

Calcium Signaling in Response to Shear

Figure 7D:
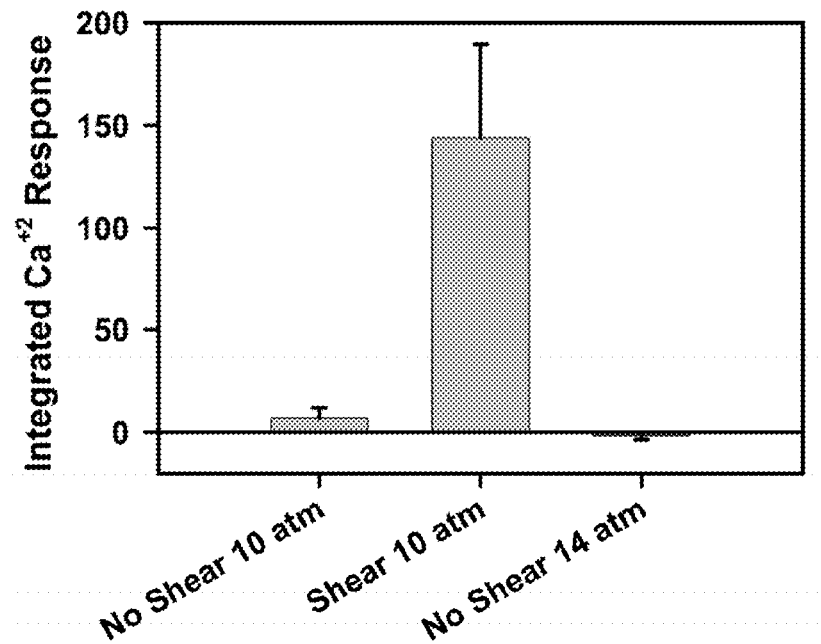
FIG. 7D shows integrated $Ca^{2+}$ Response, integral of $\Delta F/F$ over time following the blast, without and with shear forces in the same well, for six pair-matched experiments (11 atm). The first blast was without shear forces. The response to a lethal peak pressure of 14 atm with no shear forces is also shown (n=10).
Figure 7E:
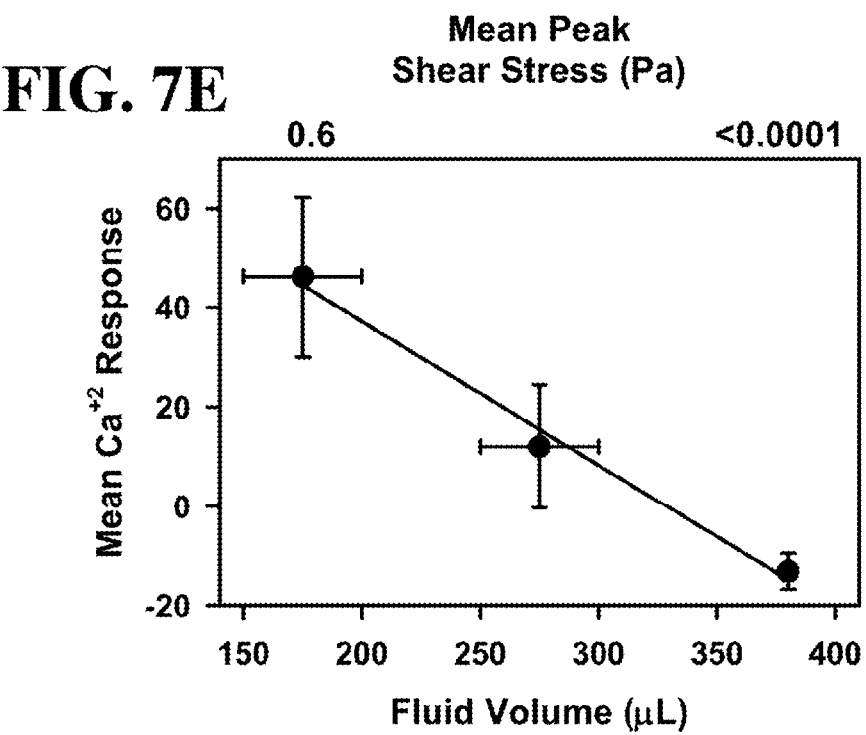
FIG. 7E is a graph of the correlation ($r^2=0.99$) between integrated $Ca^{2+}$ response following a 11 atm peak pressure blast and well fluid volume for the 3 volume conditions evaluated; 150-200, 250-300, and 380 µl with n=14, 7 and 25, respectively. Fluid volume and $Ca^{2+}$ response error bars are the range and SEM, respectively.

Cellular calcium signaling was only observed following a blast in the presence of shear. Fields of cells were subjected to blast with a peak pressure of 11 atm first in the absence and then in the presence of shear (FIGS. 7A and 7B). Increases in calcium signaling, evaluated using Fluo-4 fluorescence intensity was only observed with shear (FIG. 7C). The average calcium response of cells first exposed to a blast without shear forces and then a blast with shear forces was significantly different ($p<0.01$, n=6; FIG. 7D). Even when peak pressure exceeded 15 atm (10 experiments), a level that is typically lethal to blast victims, cellular signaling was not observed in the absence of shear (FIG. 7D). The mean calcium response increased with shear force (FIG. 7E).

The role of cellular injury was tested by subjecting cells to blasts with shear in the presence of 100 μm calcein. After controlling for pre-labeling as subsequently described, the appearance of labeled cells following a blast was evaluated in an ~6.25 mm² area containing ~2,000 cells. Two types of injured cells were observed; 1) in 2/12 experiments calcein-permeabilized cells along the edge of a cell lifted region and having a labeling pattern analogous to our positive control, scratch wounding, and 2) in 12/12 experiments a few individual calcein-permeabilized cells in an otherwise unperturbed area of the image field. The average number of individual cells wounded in the total area was 2.33 suggesting a low probability event that can be described by Poisson statistics; the observed frequency distribution is not significantly different from the Poisson distribution with parameter 2.33 ($\chi^2$, $p=0.05$).

Figure 8A:
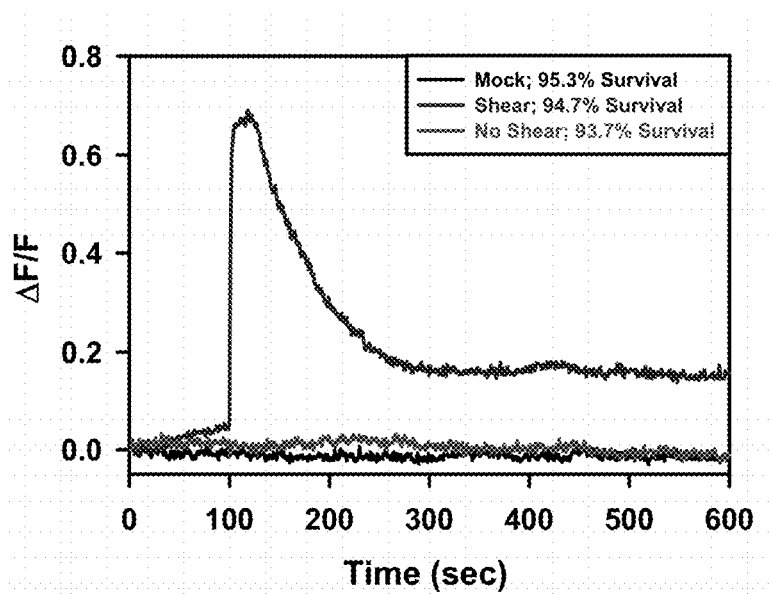
FIG. 8A is a graph illustrating cell survival is independent of blast conditions; $\Delta F/F$ for three examples of blast conditions, with and without shear and mock, no blast; survival at 20 hours was comparable for all three conditions, greater than ~94%.
Figure 8B:
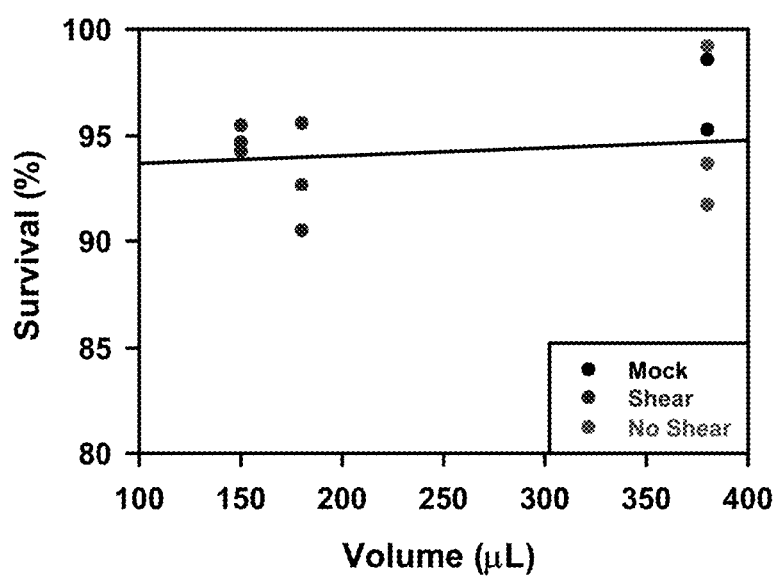
FIG. 8B shows the mean survival at 20 hours, evaluating 9,120 cells, was 94.7%+/−2.6% and ranged from 91.7%-99.2% with no correlation between survival and shear or blast (n=11 experiments).

Conventional MRI images of victims suffering from mild bTBI show no regions of necrosis or edema [Huang et al., *Journal of Neurotrauma* 26:1213-1226 (2009)] suggesting that acute cell death is not the cause of the observed bTBI symptoms. We analyzed the correlation between calcium load and cell survival for a period up to 20 hours following blast exposure with survival evaluated 20 hours after the blast. There was no correlation between cell survival and blasts with or without shear forces; the regression slope is not significantly different from zero, $p<0.01$ (FIG. 8B), nor was survival altered in two mock experiments (380 μl volume but no blast) which were not statistically different from the mean survival of all blasts, $p<0.01$. The mean survival at 20 hours, evaluating 9,120 cells, was 94.7%+/−2.6% and ranged from 91.7%-99.2% (n=11 experiments).

Example 3

Cell Culture

Optical coverslip bottomed 96 well plates (Granier) were threaded using a 1/16 NPT tap. The 96 well plates were coated with collagen at a 3 mg/ml concentration. h Vitrogen™ (Cohesion, Palo Alto, Calif.) [now available as PureCol from Advanced BioMatrix). The Vitrogen™ coated plates were then coated with poly-D-lysine (Sigma-Aldrich). Primary, human central nervous system (CNS) tissue, weeks 19-21, from elective abortions (according to NIH IRB Exempt #5116 under approved protocols) was dissociated using gentle titration in HBSS, centrifuged, washed and resuspended in neurobasal medium (NB) supplemented with B27 (Invitrogen). Cells were plated at a density of 50,000/well in NB+B27; half of the media volume was changed twice a week. Cells cultured for 2 to 5 weeks were used in all experiments.

Example 4

Imaging System

The real time imaging system is a Ti wide-field inverted microscope with Perfect Focus (Nikon, Inc.) equipped with an EM camera (Andor Technology DU-897E) running NIS Elements (Nikon, Inc.) for data acquisition and experimental control. A 20× air objective (NA 0.75) was used for imaging, but a 60× or oil immersion lenses can also be used. The fluorescence indicator, Fluo-4 (Invitrogen) was used to monitor intracellular calcium. Fluo-4 was excited using 480 nm light (Chroma HQ 480/40 nm filter) and fluorescence emission collected (Chroma HQ 535/50 nm filter) during an exposure time of 80-100 msec. The image acquisition rate was 1 Hz. An external isolation box (Oko Lab) maintained temperature (37° C.) and blocked ambient light. A ninety-six well plate was mounted on the microscope stage using a custom clamp that securely fixed the plate to the stage to avoid vibration in response to the simulated explosive blast. The microscope condenser was removed to allow access for connecting the pneumatic device to the 96 well plates.

Example 5

Calcium Imaging

Before each experiment, cells were loaded in the incubator with 6 μm Fluo-4 AM in NB+B27 and maintained at 37° C. with 95% air and 5% $CO_2$ for 30 minutes. At the end of the loading period, the cells were washed twice with NB+B27. An additional wash to final well volume was done prior to imaging each well. Prior to initiating blast experiments, the covers of the 96 well plates were replaced by a gas tight film (TSS-RTQ-100 EXCEL Scientific) sealing the wells of the plate, preserving the gas environment inside each well. The 96 well plate cover was replaced with film in a hood and elevated using a plastic spacer attached to a wire. When placed back in the incubator and equilibrated, the wire was used to remove the spacer allowing the film to fall and seal the 96 well plate. Upon removal from the incubator, the film was tightly secured prior to mounting in the microscope. The 96 well plate was attached securely to the motorized stage of the microscope.

For each experiment, a single well was centered in the microscope's field of view over the aperture in the motorized stage; the piece of film covering that well was cut and removed without affecting the sealing of the other wells; a third wash established final well volume. The T-connector 28 (FIG. 3B) was then screwed into the well 58 using the previously tapped threads. The high-pressure tubing was attached to the T-connector using a quick release connection 18, 24. A quick release valve filter was secured in the T-connector with the other end of the high-pressure hose attached to the pneumatic device (air gun 14). Baseline images were collected every second for 100 seconds and recorded. The blast was triggered after the 100$^{th}$ image while continuously imaging the well for 10 minutes. Calcium signaling was evaluated over the entire field of view by averaging fluorescence, $\Delta F/F$ as a function of time and then integrating the area under the $\Delta F/F$ curve for each experiment.

Example 6

Pneumatic Device for Generating Blast Shock Wave

The pneumatic device 10 (FIGS. 1 and 4) uses an air gun (Airforce Model R9901) that was modified by Axiom/Lemak (Virginia). Modifications included replacing the gun barrel with an 8-inch tube having a high-pressure hose quick connection, modifying the hammer and the spring mechanism that controls the hammer trigger, and changing the gas tank valve. The gas mixture in the pneumatic device, which was pressurized to 1500 psi, was 95% air and 5% CO2. To simulate an open field blast the T-connector externally threaded leg 30 was threaded vertically into the corresponding internal threads of the well while the internally threaded arms ran horizontally above the well (FIG. 3B). Arm 28a was attached to the high-pressure hose while the other arm 28b was used for the release valve.

To simulate an explosive blast, a quick release valve 32 was used. The simple and reproducible quick release valve was a filter plug taken from a 1250 µl pipette tip (Thermo Scientific) that was inserted into the threads of the internally threaded arm 28b. Using ⅙-1¼ turns resulted in 6-15 atm peak overpressure above ambient pressure. A ⅙ turn produced 6 atm peak overpressure, while 1¼ turns provided 15 atm peak pressure. The quick release valve was preferred as compared to a fixed pressure release valve with a significantly longer rise time. When the air gun trigger was pulled, the device was activated, releasing a burst of pressurized gas from the tank. As the pressurized gas was released, the quick release valve on the T-connector trapped gas and a rapid increase in pressure was created within the well. When the pressure exceeded the limit of the quick release valve the plug was ejected, allowing the gas to escape, and resulting in a rapid decay of overpressure as the accumulated pressure was released. The rapid gas flow through the narrow horizontal portion of the T-connector creates a drop in pressure in the well (Venturi effect), to below ambient levels.

Example 7

Measurement of Simulated Blast Parameters

To measure the simulated blast parameters, a mock 96 well chamber (FIG. 3C) was constructed and threaded with the same tap used on the 96 well plate. Fiber optic pressure sensors (FISO Technologies FOP-MIV-BA-C1-F1-M2-R3-ST (0-150 PSI) or FOP-MEMs-1000PSI) were mounted in a hole in the bottom of the mock-chamber. The sensor was connected to a Veloce 50 controller (FISO Technologies) with a bandwidth of 200 kHz; pressure responses were displayed and recorded using a digital oscilloscope (Tektronix TDS 754D). This pneumatic device is capable of generating waveforms with high reproducibility, as demonstrated by the standard errors. Once the pressures are calibrated using the device shown in FIG. 3C, the device can coupled to a chamber (such as well 58) for experiments with target tissue in the absence of pressure monitoring.

Example 8

Injury Analysis

In order to evaluate cell injury following a blast, calcein (Invitrogen) uptake was measured. Cells were plated as described, incubated with 100 µM calcein for 5 min., and washed 4 times. Calcein was imaged using the Fluo-4 settings. An area of ~6.25 mm$^2$ was imaged by tiling 49 regions (7×7 grid) in order to establish the pre-blast level of calcein labeling. 100 µM calcein was added back to the well and the cells subjected to blast with or without shear and incubated for another 5 min. The cells were washed 4× on the microscope and the same area reimaged. The paired images were background subtracted, aligned, color coded for pre and post blast, and the appearance of new calcein labeled cells was determined. The positive control was scratch wounding the cell layer; cells and cell processes along the scratch were labeled. The negative control was blast without shear; no additional labeling was observed.

Example 9

Survival Analysis

In order to evaluate cell survival following a blast, a dual color staining of nuclei was used to differentiate between cells that were dead before the blast and those cells that died during the 20 hours after the blast. Cells were loaded with 6 µm Fluo-4 µM for 30 minutes, washed with NB+B27 containing 0.5 µM ethidium homodimer-1 (Invitrogen) in order to stain existing dead cells, incubated for 5 minutes and then washed 3 times with NB+B27. Wells were set with different volumes of NB+B27 in order to establish conditions for a blast with (150 and 180 µl) and without shear (3800. Following the blast protocol, the 96 well plate was maintained on the microscope in a custom designed chamber (Precision Plastics, MD) that was maintained at 37° C. and 95% air 5% $CO_2$. Twenty hours after a blast the cells were labeled with 6 Fluo-4 AM for 30 minutes, and then 0.5 µg/ml DAPI for 5 minutes in order to identify newly dead cells, washed 2× with NB+B27, and every area previously imaged was reimaged. A total of 25 areas were tiled for every well. The conditions for Fluo-4 imaging were those described previously. DAPI was excited using 350 nm light (Chroma AT 350/50 nm filter) and fluorescence emission collected (Chroma D460/50 nm filter). Ethidium Homodimer-1 was excited using 545 nm light (Chroma HQ 545/30 nm filter) and fluorescence emission collected (Chroma HQ 620/60 nm filter).

ImageJ was used for all image processing. The ethidium homobromide-1 channel (red) and the DAPI channel (blue) were background subtracted, filtered using 2 pixels Gaussian blurring, and a binary image created using Otsu threshold. The binary images were color-coded using red and blue look up tables and merged into one image. Newly dead cells were identified as having nuclei uniquely blue while all previously ethidium homobromide-1 labeled nuclei appeared magenta (blue+red). The merged images were color threshold and the remaining blue nuclei counted using Analyze Particles with the following settings: size 25—infinity (pixel$^2$), circularity 0.85-1.00, and exclude on edges. Images were background subtracted, filtered using 2 pixels Gaussian blurring, and Otsu threshold. Cells were counted using Analyze Particles with the following settings: size 100—infinity (pixel$^2$), circularity 0-1.00, and exclude on edges. The total cell count was the sum of newly dead cells (uniquely blue nuclei) and the Fluo-4 cell count. The survival fraction at 20 hours is expressed as the ratio of blue nuclei to the total cell count (Fluo-4 cell count+ uniquely blue nuclei).

Example 10

Shear Analysis

To estimate the shear stress produced by the pressure pulse, 6 μm InSpeck fluorescent component E microspheres (beads) were added to identical 96 well plates containing phosphate buffered saline (PBS); conditions, such as temperature and relative positions in the chambers were the same as in the cell experiments. During acquisition of a continuous series of frames with 400 ms exposure time each, the pressure pulse was applied to wells with different fluid volumes. The trajectory of a moving bead appears in one of the frames as a continuous curve of varying intensity (see FIG. 6). The position-dependent brightness of a particular track is inversely proportional to the bead velocity along the track. The exposure time and camera gain were selected guided by three main goals: capturing the bead movement in one frame, detecting sufficient light during the highest bead velocity, and minimizing camera saturation at low velocities. The correlation between light intensity and exposure time is calculated by averaging the intensities of static beads using different exposure times in the range of 10 ms-400 ms. This calibration is used to convert intensities of the moving beads into time units and define the arc length (i.e., the distance along the trajectory) of the bead trajectories over time.

The velocity is derived using the first derivative of the arc length with respect to time. An approximate linear relation between the flow velocity and separation z from the surface is then used to estimate the shear stress. The main assumptions are: (i) the beads move together with the liquid (i.e., Brownian motions are negligible); (ii) the shear stress sensed by a cell is only due to the flow of media that is close to the chamber surface, z<6 μm; (iii) the beads used to evaluate flow have a quasi-two dimensional path (i.e., move mostly in the x-y plane and not the z-direction). In all experiments analyzed there is a clear correlation between trajectories of the moving beads, justifying the assumption that for short time periods after the blast the beads move together with the surrounding liquid. However, the bead trajectory characteristics varied; in some experiments the trajectories were three-dimensional with beads moving out of the focal plane. This behavior may be related to turbulence. Even when most beads moved, a few beads exhibited little or no movement. This behavior may be related to strong surface adhesion. Images were processed with ImageJ (NIH) and analyzed with Origin 8.51.

Determining Shear Stress

Figure 9:
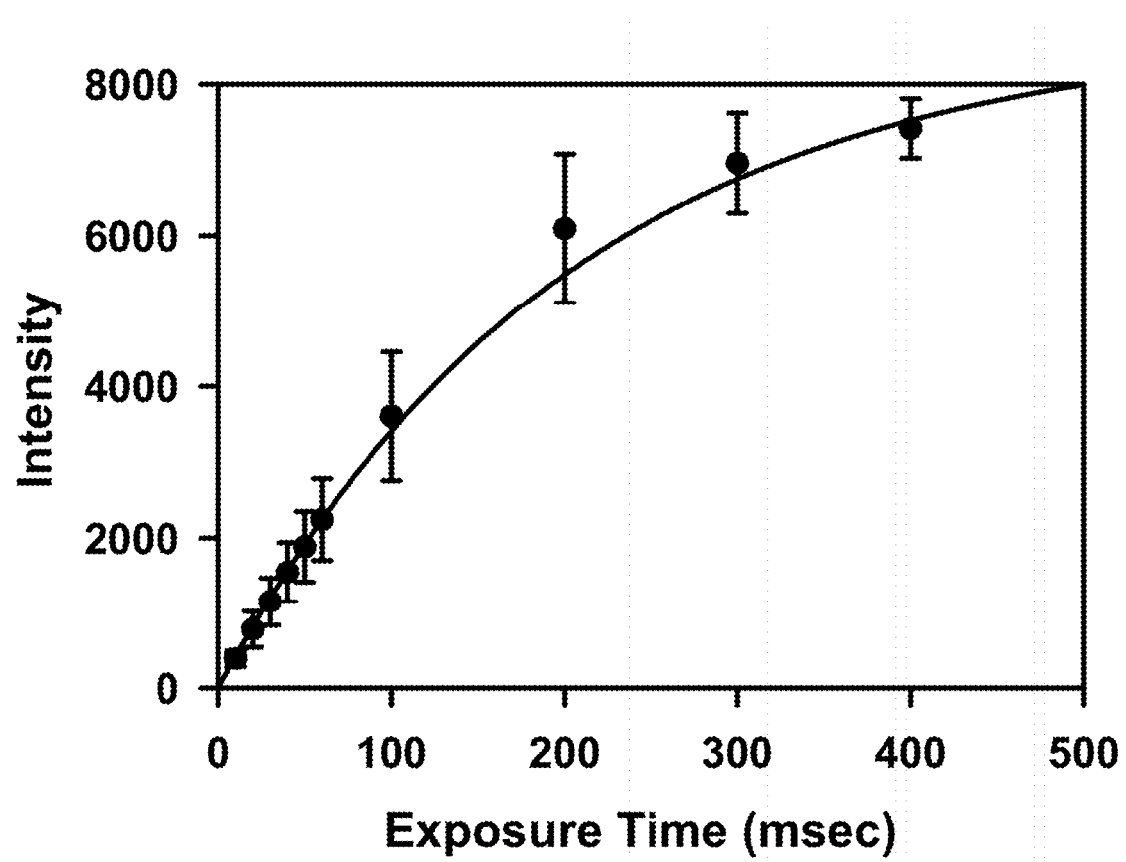
FIG. 9 is a graph illustrating stationary bead intensity as a function of exposure time. Error bars are standard deviations, and the solid line is the best fit to $I=a(1-e^{-b\Delta t})$ (equation 1) with $a=(8.73\pm0.25)\times10^3$ and $b=(4.95\pm0.29)\times10^{-3}$.

Calibration:

Frames of resting beads were taken at various exposure times between 10 ms and 400 ms. After Gaussian smoothing and "Rolling Ball" background subtraction the fluorescence intensity of each bead was measured from the center of mass (i.e., the pixels of highest intensity). As expected, it was found that the relations between the intensity (I) and exposure time (Δt) are linear for short time scales but begin to saturate at longer time scales. FIG. 9 shows the averaged intensities versus exposure time for 24 beads. These values are fit to the asymptotic function $$I = a(1 - e^{-b\Delta t}), \quad \text{Eq. (1)}$$

with fitting parameters $a = (8.73 \pm 0.25) \times 10^3$ and $b = (4.95 \pm 0.29) \times 10^{-3}$; note, for short exposures, $\Delta t \ll 1/b$, the relation between intensity and time is linear.

Analyzing Bead Trajectories:

After Gaussian smoothing and "Rolling Ball" background subtraction, the frame with the most significant displacements was selected, and the bead trajectories were analyzed (see FIG. 6). Trajectories with overlaps were not evaluated. The basic data, illustrated in FIG. 10A, were obtained as intensity versus distance along the trajectory S of one of the trajectories in FIG. 6. Since a bead moves, each pixel accumulates signal from more than one point and therefore the intensity was rescaled as: $I \to (\xi/d)I$ where $\xi$ is the pixel size (≈1.4 μm) and d is the bead's diameter (6 μm). The time a bead spent in one spot, was calculated by inverting the function in Eq. (1):

$$\Delta t_n = \frac{1}{b} \ln\left(\frac{1}{1 - I/a}\right) \quad \text{Eq. (2)}$$

The time it takes the bead to move to the $n^{th}$ pixel was defined as:

$$t_n = \sum_{i=1}^{n} \Delta t_i, \quad \text{Eq. (3)}$$

and the time-dependent trajectory length S (t) was then numerically constructed (FIG. 10B). The velocity function was found as the first derivative of the trajectory length $$v(t) = \frac{\partial S(t)}{\partial t}. \quad \text{Eq. (4)}$$

The shear stress in liquid medium above the surface is defined as $$\tau = \mu \frac{\partial v}{\partial z}, \quad \text{Eq. (5)}$$

where z is the height above the surface and μ is the medium viscosity. Assuming a linear growth of the velocity near the surface, with the velocity at the surface equal to zero, we estimated the shear stress as $$\tau(t) = \mu \frac{v(t)}{0.5d}. \quad \text{Eq. (6)}$$

The two characteristics, v(t) and τ(t), of the shear flow obtained in one of the blasts with shear are plotted in (FIG.

10C, thick dark curve). Four additional examples of the velocity and shear stress are shown in FIG. 10C.

The results disclosed herein show that human brain cells in culture are indifferent to blast induced fast transient pressure waves (BSW) consisting of sub-msec rise time, positive peaks of up to 15 atm, followed by tensions of 0.2 atm, of msec total duration. Furthermore, the cells only respond with global elevations in intracellular free $Ca^{2+}$ when sufficient shear forces are simultaneously induced with the pressure profiles. These results makes it unlikely that the primary effect of a blast shock wave on brain cells in vivo is a direct effect of the compression and tension forces created by the pressure transient per se. However, the observed correlations between cellular response and shear forces, and the lack of correlation to pressure, per se, suggest that shear forces are likely involved in the primary injury phase of bTBI.

The human brain, in its bony skull, is a complex system with multiple inhomogeneities, through which pressure waves travel at different speeds. It is this difference in speed that creates shear, potentially between brain cells. Depending on the orientation of their CNS tissues with the blast propagation, different shear forces may develop and the shockwave may encounter membrane interfaces with different susceptibility to damage. Thus, this is in agreement with observations both in in vivo models, as well as with human injuries in which expression of bTBI symptoms among different individuals that are exposed to the same blast is heterogeneous.

Cells survive shear stresses up to 14 Pa with 20 msec and longer rise times but permeability of their membranes to soluble dyes and electrical activity is altered in neuronal cultures. Homogenization of brain tissue begins with a power driven pestle creating macroscopic shearing that we estimate at ~10 Pa. Yet such shear forces are insufficient to detach the pre-synaptic terminal from the post-synaptic terminal, thus the adhesion of the interneuronal junction surpasses that of cellular membrane integrity, and the tubular necks of membrane that attach the synapse to the axon, dendrite or cell body preferentially rupture instead, yielding the synaptosome. These properties of the synaptosome preparation suggest that shear stress acts directly at the cell membrane. Thus, it is more likely that the primary injury of bTBI involves a direct rupture of the cell membrane, resulting in calcium entry, rather than a direct disruption of neuronal connectivity. Cell injury is often followed by swelling, which may secondarily disrupt connectivity.

Calcium has been implicated in the induction of neuronal death during TBI and stroke; calcium is elevated for long periods of time (days, in cells surviving TBI and stroke). The results shown herein demonstrate that calcium is elevated transiently for short periods of time (seconds to a few minutes), and cell death does not occur even after 20 hours following this excitation. Brain cells exposed to blast wave profiles lacking shear forces had no calcium response, even at peak pressures up to 15 atm and trough pressures of 0.2 atm, suggesting that a shear dependent mechanism of primary bTBI may involve mechano-sensitive channels, lipidic pores, or uniquely vulnerable regions of the neuronal plasma membrane, leading to activation of a small population of cells and subsequent amplification through cell-cell signaling. The high curvature stress at the necks of pre-synaptic and post-synaptic boutons or fine processes of astrocytes may be an example of vulnerable regions since the curvature stress would add to the shear stress at those points, known to disassemble during homogenization.

Using primary human brain cell cultures at the level of single and small networks of cells, we found that shear forces acting at cellular length scales, rather than changes in pressure per se control the major activation parameter of CNS derived cell culture, intracellular calcium. Rapid compression and positive tension alone do not appear to cause calcium dependent cell-cell signaling following a BSW. This is one example of the usefulness of the device and methods disclosed herein for studying the response of cells to blast shock waves.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A device for simulating an explosive blast shock wave, comprising:
    a source of compressed gas;
    a primary conduit conveying gas from the source of compressed gas along a primary axis of gas flow, wherein the primary conduit comprises a release valve that opens when gas pressure at the release valve reaches a predetermined pressure;
    a secondary conduit extending at an angle to the primary conduit axis of gas flow, wherein the secondary conduit terminates in an outlet orifice that directs gas from the primary conduit toward a target region, and the secondary conduit exits the primary conduit between the source of compressed gas and the release valve;
    a trigger releasing the compressed gas into the primary conduit toward the release valve to generate a simulated blast shock wave flow of gas through the outlet orifice, wherein a pressure amplitude of the blast shock wave increases until the release valve in the primary conduit opens and reduces pressure in the secondary conduit and at the outlet orifice;
    a specimen platform positioned adjacent the outlet orifice.

2. The device of claim 1, wherein the secondary conduit is perpendicular to the primary conduit, such that opening of the release valve in the primary conduit rapidly reduces pressure in the secondary conduit to generate negative ambient pressure at the outlet orifice.

3. The device of claim 1, further comprising an imaging device adjacent the specimen platform that is capable of capturing images of a specimen on the specimen platform to determine response of the specimen to the blast shock wave.

4. The device of claim 3, wherein the imaging device comprises a microscope positioned to capture images from the specimen chamber.

5. The device of claim 4, further comprising a transparent specimen chamber on the specimen platform for containing a specimen on the specimen platform, and wherein the microscope is positioned to view the specimen from below the platform.

6. The device of claim 1 wherein the quick release valve comprises a plug that is ejected from the primary conduit when pressure at the outlet orifice reaches a predetermined value.

7. The device of claim 5, further comprising a specimen coupling that forms a gas-tight seal between the outlet orifice and the transparent specimen chamber.

8. The device of claim 7, wherein the specimen coupling comprises threads on the secondary conduit that mate with threads on the transparent chamber.

9. The device of claim 3 wherein the specimen platform is movable to position specimens relative to the imaging system.

10. The device of claim 4, further comprising a biological specimen in the specimen chamber, wherein the specimen comprises a cellular preparation or tissue sample obtained from an animal.

11. The device of claim 10, wherein the cellular preparation or tissue sample consists of nerve cells.

12. The device of claim 5 further comprising the specimen, wherein the specimen is a layer of cells on a bottom of the chamber, and a layer of liquid covers the cells.

13. The device of claim 1, wherein the simulated blast shock wave at the outlet orifice increases from ambient pressure to at least 4 atm maximum amplitude pressure and decreases to below ambient pressure, in less than about 0.5 milliseconds.

14. A device for simulating an explosive blast shock wave, the device comprising:
a source of compressed gas;
a primary conduit for conveying gas from the source of compressed gas along a linear primary conduit axis of gas flow, wherein the primary conduit axis of gas flow terminates in a T-outlet having distal and proximal arm portions through which the linear primary conduit axis extends, and a leg portion extending perpendicular to the linear primary conduit axis between the distal and proximal arms to form a secondary conduit terminating in an outlet orifice through which a simulated blast shock wave is emitted, wherein the distal arm of the T-outlet is occluded with an occlusion member that selectively opens the distal arm of the T-outlet to the flow of compressed gas to the atmosphere when gas pressure at the occlusion member reaches a preselected pressure; a trigger member for selectively releasing the compressed gas into the primary conduit to generate a flow of gas through the primary conduit to the T-outlet, and out of the outlet orifice to initiate the simulated blast shock wave, until the preselected pressure at the occlusion member is reached and the occlusion member is opened to permit the compressed gas to flow out of the distal arm of the T-outlet instead of the outlet orifice, whereby compressed gas flowing through the primary conduit axis reduces gas pressure in the leg of the T-outlet and at the outlet orifice, wherein the simulated blast shock wave at the outlet orifice increases from ambient pressure to at least 4 atm maximum amplitude pressure and decreases to below ambient pressure in less than about 0.5 milliseconds.

15. The device of claim 14, further comprising a specimen platform positioned at a location that is impinged by the simulated blast shock wave as the blast shock wave is emitted through the outlet orifice, and an imaging device for viewing the specimen on the specimen platform as the simulated blast shock wave from the outlet orifice impinges the specimen.

16. The device of claim 15, further comprising a specimen chamber on the specimen platform and a coupling that seals the leg portion of the T-outlet to the specimen chamber.

17. The device of claim 16, wherein the coupling comprises mating threads on the leg of the T-outlet and the specimen chamber.

18. The device of claim 15, wherein the specimen platform is movable to a plurality of positions at which different specimens are positioned at a location to be impinged by the simulated blast shock wave and imaged by the imaging device.

19. The device of claim 16, further comprising a biological target specimen in the specimen chamber.

20. The device of claim 15, wherein the imaging device comprises a recording device for recording the specimen as it is exposed to the blast shock wave.

21. The device of claim 20, wherein the imaging device comprises a microscope.

22. A method of assessing a response of tissue or cells to a simulated blast shock wave using the device of claim 5, comprising:
providing a specimen in a specimen chamber on the specimen platform;
activating the trigger for selectively releasing the compressed gas into the primary conduit to generate a flow of gas through the primary conduit and out of an outlet orifice to produce the simulated blast shock wave that impinges the specimen in the specimen chamber;
observing the effect of the blast shock wave on the specimen in the specimen chamber.

23. The method of claim 22, wherein the specimen is a tissue or cellular preparation.

24. The method of claim 22, wherein the specimen chamber further includes a liquid over the biological specimen.

25. The method of claim 23, wherein the specimen chamber comprises a well of a multi-well plate, and the multi-well plate is moved to position a well of the multi-well plate where the simulated blast shock wave impinges the specimen and is imaged by the imaging device.

26. The method of claim 24, wherein the chamber is sealed to the secondary conduit to communicate only with the outlet orifice.

27. The method of claim 22, wherein the imaging device comprises an imaging system that records images of the specimen as it is impinged by the blast shock wave.

28. The method of claim 27, wherein the imaging system comprises a microscope for observing microscopic effects of the blast shock wave on the specimen in the specimen chamber.

29. The method of claim 24, further comprising varying shear forces on the specimen by varying a depth of the liquid in the chamber over the specimen.

30. The method of claim 24 wherein the specimen is in a cell plane, and shear force at the cell plane is measured by observing movements of fluorescent beads in the cell plane.

31. The method of claim 22, wherein the specimen is nerve tissue.

32. The method of claim 31, wherein the cells are dissociated cells from the central nervous system.

* * * * *